(12) United States Patent
Freyssinet et al.

(10) Patent No.: US 6,770,798 B1
(45) Date of Patent: Aug. 3, 2004

(54) NUCLEIC ACID SEQUENCES CODING FOR THANATIN AND TRANSFORMED PLANTS CONTAINING THEM

(75) Inventors: Georges Freyssinet, Saint Cyr au Mont d'OR (FR); Richard Derose, Evry (FR); Jules Hoffmann, Strasbourg (FR)

(73) Assignee: Aventis Cropscience, Lyons (FR)

( * ) Notice: Subject to any disclaimer, the term of this patent is extended or adjusted under 35 U.S.C. 154(b) by 0 days.

(21) Appl. No.: 09/554,024

(22) PCT Filed: Nov. 6, 1998

(86) PCT No.: PCT/FR98/02375

§ 371 (c)(1),
(2), (4) Date: Oct. 16, 2000

(87) PCT Pub. No.: WO99/24594

PCT Pub. Date: May 20, 1999

(30) Foreign Application Priority Data

Nov. 7, 1997 (FR) ............................................ 97 14263

(51) Int. Cl.⁷ ........................ C12N 15/09; C12N 15/31; C12N 15/82; A01H 5/00; A01H 5/10
(52) U.S. Cl. ....................... 800/279; 800/278; 800/288; 800/298; 800/295; 435/320.1; 435/419; 435/468; 536/23.7
(58) Field of Search ................................. 800/279, 278, 800/288, 298, 295, 294; 435/320.1, 419, 468, 69.7; 536/237, 23.6, 24

(56) References Cited

U.S. PATENT DOCUMENTS 5,597,946 A * 1/1997 Jaynes et al. ................ 800/205

FOREIGN PATENT DOCUMENTS

| EP | 0798381 | 10/1997 |
| FR | 2732345 | 10/1996 |
| FR | 2733237 | 10/1996 |

OTHER PUBLICATIONS

Ryals et al, "Systemic Acquired Resistance", 1996, The Plant Cell, vol. 8, pp. 1809–1819.*
Broun et al, "Catalytic Plasticity of Fatty Acid Modification Enzymes Underlying Chemical Diversity of Plant Lipids", Nov. 1998, Science vol. 282, pp. 1315–1318.*
Lazar et al, "Transforming Growth Factor x:Mutation of Aspartic Acid 47 and Leucine 48 Results in Different Biological Activities", Molecular and Cellular Biology, Mar. 1988, 1247–1252.*
Fehlbaum et al. (1994) Journal of Biological Chemistry 269:52.
Fehlbaum et al. (1996) Proc. Natl. Acad. Sci. USA 93: 1221.

* cited by examiner

*Primary Examiner*—Elizabeth F. McElwain
*Assistant Examiner*—Medina A. Ibrahim
(74) *Attorney, Agent, or Firm*—Baker Botts L.L.P.

(57) ABSTRACT

The invention concerns a nucleic acid sequence coding for thanatin, a vector containing it for transforming a host, and plants and plant cells transformed by the nucleic acid.

25 Claims, 5 Drawing Sheets

NUCLEIC ACID SEQUENCES CODING FOR THANATIN AND TRANSFORMED PLANTS CONTAINING THEM

The subject of the present invention is a DNA sequence encoding thanatin, a vector containing it for the transformation of a host organism, and the method of transforming the said organism.

The invention relates more particularly to the transformation of plant cells and plants, the thanatin produced by the transformed plants conferring on them resistance to diseases, in particular of fungal origin.

An increasing need already exists for making plants resistant against diseases, in particular fungal diseases, in order to reduce, or even eliminate, the need for treatment with antifungal protection products, with a view to protecting the environment. One means of increasing this resistance to diseases consists in transforming the plants so that they produce substances capable of providing their defence against these diseases.

Various substances of natural origin, in particular peptides, are known which exhibit bactericidal or fungicidal properties, in particular against the fungi responsible for plant diseases. However, the problem consists in finding such substances which not only can be produced by transformed plants, but can still preserve their bactericidal or fungicidal properties and confer them on the said plants. For the purposes of the present invention, bactericidal or fungicidal is understood to mean the actual bactericidal or fungicidal properties and the bacteriostatic and fungistatic properties.

Thanatin is a peptide produced by bacterial induction on adult Psodius sp, preferably *maculiventris*. Its preparation by bacterial induction is described in patent application FR 2,733,237, as well as its antifungal and antibacterial properties in vitro.

After having first identified the thanatin gene, it was also found that it could be inserted into a host organism, in particular a plant, in order to express the thanatin and confer on the said host organism properties of resistance to fungal diseases and to diseases of bacterial origin, providing a particularly advantageous solution to the problem stated above.

The subject of the invention is therefore first a nucleic acid fragment encoding thanatin, a chimeric gene comprising the said fragment encoding thanatin as well as heterologous regulatory elements at the 5' and 3' positions which can function in a host organism, in particular in plants, and a vector for transforming the host organisms containing this chimeric gene, and the transformed host organism. It also relates to a transformed plant cell containing at least one nucleic acid fragment encoding thanatin and a disease-resistant plant containing the said cell, in particular regenerated from this cell. It finally relates to a method of transforming plants to make them resistant to diseases, in which method a gene encoding thanatin is inserted by means of an appropriate vector.

Thanatin is understood to mean according to the invention any peptide comprising essentially the peptide sequence of 11 amino acids which is described in patent application FR 2,733,237, as well as the equivalent homologous sequences in which certain amino acids are replaced by different but equivalent amino acids at sites which do not induce substantial modification of the antifungal or antibacterial activity of the said homologous sequence. Peptide sequence comprising essentially the peptide sequence described in patent application FR 2,733,237 is understood to mean not only the sequence defined by the sequence identifier No. 1 (SEQ ID NO 1), but also such a sequence comprising at either of its ends, or at both, peptide residues necessary for its expression and targeting in a host organism, in particular a plant cell or a plant.

Thanatin is a peptide of formula (I)(SEQ ID NO:14):

Xaa-Ile Ile Tyr Cys Asn Arg Arg Thr Gly Lys Cys-Xab    (I)

in which:

Xaa is $NH_2$ or a variable residue having a sequence comprising from 1 to 10 amino acids, and Xab is OH or a variable residue having a sequence comprising from 0 to 5 amino acids.

Advantageously, when Xaa comprises at least one amino acid, the latter is one of the 20 base amino acids and more particularly chosen from the group comprising Gly, Ser, Lys, Pro and Val. When Xab comprises at least one amino acid, the latter is one of the 20 base amino acids and more particularly chosen from the group comprising Gln, Arg and Met.

According to a preferred embodiment of the invention, the two cysteine residues of the peptide of formula (I) form an intramolecular disulphide bridge.

The present invention therefore relates first to a nucleic acid, in particular a DNA, fragment encoding the thanatin defined above. It may be, according to the invention, a fragment isolated from Psodius sp, preferably *maculiventris*, or alternatively a derived fragment, suitable for the expression of thanatin in the host organism where the peptide will be expressed. The nucleic acid fragment may be obtained using standard methods of isolation and purification, or alternatively by synthesis according to the customary techniques of successive hybridizations of synthetic oligonucleotides. These techniques are in particular described by Ausubel et al.

According to the present invention, "nucleic acid fragment" is understood to mean a nucleotide sequence which may be of the DNA or RNA type, preferably of the DNA, in particular cDNA, especially double-stranded, type.

According to one embodiment of the invention, the nucleic acid fragment encoding thanatin comprises the DNA sequence described by the sequence identifier No. 1 (SEQ ID NO 1), a homologous sequence or a sequence complementary to the said sequence.

Advantageously, the nucleic acid fragment according to the invention comprises the DNA sequence described by the sequence identifier No. 2 (SEQ ID NO 2), a homologous sequence or a sequence complementary to the said sequence.

"Homologous" is understood to mean according to the invention a nucleic acid fragment having one or more sequence modifications relative to the nucleotide sequence described by the sequence identifier No. 1 or No. 2 and encoding thanatin. These modifications may be obtained according to the customary mutation techniques, or alternatively by choosing the synthetic oligonucleotides used in the preparation of the said sequence by hybridization. Given the multiple combinations of nucleic acids which may lead to the expression of the same amino acid, the differences between the reference sequence described by the sequence identifier No. 1 or No. 2 and the homologue may be great, especially since a DNA fragment of less than 100 nucleic acids in size, which can be produced by synthesis, is involved. Advantageously, the degree of homology will be at least 70% relative to the reference sequence, preferably at least 80%, more preferably at least 90%. These modifications are generally neutral, that is to say that they do not affect the primary sequence of the resulting thanatin.

The present invention also relates to a chimeric gene (or an expression cassette) comprising a coding sequence as well as heterologous regulatory elements at the 5' and 3' positions which can function in a host organism, in particular plant cells or plants, the coding sequence comprising at least one DNA fragment encoding thanatin as defined above.

Host organism is understood to mean any higher or lower mono- or pluricellular organism into which the chimeric gene according to the invention may, be introduced, for the production of thanatin. It consists of in particular bacteria, for example *E. coli*, yeasts, in particular of the genera Saccharomyces or Kluyveromyces, or preferably plant cells and plants. "Plant cell" is understood to mean according to the invention any cell derived from a plant and which may constitute undifferentiated tissues such as calli, and differentiated tissues such as embryos, plant portions, plants or seeds.

"Plant" is understood to mean according to the invention any differentiated multicellular organism capable of photosynthesis, in particular monocotyledones or dicotyledones, more particularly cultivated plants intended or otherwise as animal feed or for human consumption, such as maize, wheat, colza, soya bean, rice, sugar cane, beet, tobacco, cotton and the like.

The regulatory elements necessary for the expression of the DNA fragment encoding thanatin are well known to persons skilled in the art depending on the host organism. They comprise in particular promoter sequences, transcription enhancers, transit peptides, terminator sequences, including start and stop codons. The means and methods for identifying and selecting the regulatory elements are well known to persons skilled in the art.

The nucleic acid fragment according to the invention may also comprise a nucleic acid sequence fused in 5' and/or 3' to the sequence encoding thanatin, so as to obtain a "protein-thanatin" fusion protein, whose cleavage by the enzymatic systems of the host organism allows the release of thanatin. This thanatin-fused protein may be a signal peptide or a transit peptide which makes it possible to control and orient the production of thanatin in a specific manner in a part of the host organism, such as for example the cytoplasm, the cell membrane, or in the case of plants in a particular type of tissue or in the extracellular matrix.

According to one embodiment, the transit peptide may be a signal for chloroplast or mitochondrial addressing, which transit peptide is then cleaved in the chloroplast or the mitochondria.

According to another embodiment of the invention, the signal peptide may be an N-terminal signal or "prepeptide", optionally in combination with a signal responsible for retaining the protein in the endoplasmic reticulum, or a peptide for vacuolar addressing or "propeptide". The endoplasmic reticulum is the site where operations of maturation of the protein produced, such as for example the cleavage of the signal peptide, are carried out by the "cellular machinery".

The invention relates more particularly to the transformation of plants. As regulatory promoter sequence in plants, there may be used any promoter sequence of a gene which is expressed naturally in plants, in particular a promoter of bacterial, viral or plant origin such as, for example, that of a gene for the small subunit of ribulose biscarboxylase (RuBisCO) or of a plant virus gene, for example that of cauliflower mosaic (CAMV 19S or 35S), or a promoter inducible by pathogens such as tobacco PR-1a or asparagus AoPRT-L, it being possible for any known suitable promoter to be used. Preferably, a regulatory promoter sequence is used which promotes the overexpression of the coding sequence constitutively or inducibly by a pathogen attack, such as for example that comprising at least one histone promoter as described in application EP 0,507,698.

According to the invention, it is also possible to use, in combination with the regulatory promoter sequence, other regulatory sequences which are situated between the promoter and the coding sequence, such as transcription enhancers such as for example the tobacco mosaic virus (TMV) translation enhancer described in application WO 87/07644, or the tobacco etch virus (TEV) translation enhancer described by Carrington & Freed, or transit peptides, either single or double, and in this case optionally separated by an intermediate sequence, that is to say comprising, in the direction of transcription, a sequence encoding a transit peptide of a plant gene encoding a plastid localization enzyme, a portion of sequence of the N-terminal mature portion of a plant gene encoding a plastid localization enzyme, and then a sequence encoding a second transit peptide of a plant gene encoding a plastid localization enzyme consisting of a portion of sequence of the N-terminal mature portion of a plant gene encoding a plastid localization enzyme, as described in application EP 0,508,909. As transit peptide, there may be mentioned the signal peptide of the tobacco PR-1a gene described by Cornelissen et al., represented with its coding sequence by the sequence identifier No 3.

The sequence encoding the fusion protein signal peptide PR-1a-thanatin and this fusion protein also form part of the present invention. This sequence is in particular described by the sequence identifier No. 5, more particularly the coding part of this sequence, corresponding to bases 12 to 164.

As regulatory terminator or polyadenylation sequence, there may be used any corresponding sequence of bacterial origin, such as for example the nos terminator from *Agrobacterium tumefaciens*, or alternatively of plant origin, such as for example a histone terminator as described in application EP 0,633,317.

According to the present invention, the chimeric gene may also comprise a selectable marker suitable for the transformed host organism. Such selectable markers are well known to persons skilled in the art. They may be a gene for resistance to antibiotics, such as penicillin, or alternatively a gene for tolerance of herbicides for plants.

The present invention also relates to a cloning or expression vector for the transformation of a host organism containing at least one chimeric gene as defined above. This vector comprises, in addition to the above chimeric gene, at least one replication origin. This vector may consist of a plasmid, a cosmid, a bacteriophage or a virus, transformed by the introduction of the chimeric gene according to the invention. Such transformation vectors, depending on the host organism to be transformed, are well known to persons skilled in the art and are widely described in the literature.

For the transformation of plant cells or plants, they may consist in particular of a virus which may be used for the transformation of developed plants and containing, in addition, its own elements for replication and expression. Preferably, the vector for transforming plant cells or plants according to the invention is a plasmid.

The subject of the invention is also a method of transforming host organisms, in particular plant cells, by integration of at least one nucleic acid fragment or a chimeric gene as defined above, which transformation may be obtained by any known appropriate means widely described in the specialist literature and in particular the references cited in the present application, more particularly by the vector according to the invention.

A series of methods consists in bombarding cells or protoplasts with particles to which the DNA sequences are attached. Another series of methods consists in using, as means of transferring into the plant, a chimeric gene inserted into a Ti plasmid from *Agrobacterium tumefaciens* or an Ri plasmid from *Agrobacterium rhizogenes*.

Other methods may be used, such as microinjection or electroporation or alternatively direct precipitation by means of PEG.

Persons skilled in the art will make the choice of the appropriate method depending on the nature of the host organism, in particular the plant cell or the plant.

The subject of the present invention is also the host organisms, in particular plant cells or plants, transformed and containing an effective quantity of a chimeric gene comprising a sequence encoding the thanatin defined above.

The subject of the present invention is also the plants containing transformed cells, in particular the plants regenerated from transformed cells. The regeneration is obtained by any appropriate method which depends on the nature of the species, as for example described in the references above.

For the methods of transforming plant cells and of regenerating plants, the following patents and patent applications may be mentioned: U.S. Pat. Nos. 4,459,355, 4,536,475, 5,464,763, 5,177,010, 5,187,073, EP 267,159, EP 604 662, EP 672 752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442,174, EP 486,233, EP 486,234, EP 539,563, EP 674,725, WO 91/02071 and WO 95/06128.

The present invention also relates to the transformed plants derived from the cultivation and/or crossing of the above regenerated plants, as well as the seeds of transformed plants.

The plants thus transformed are resistant to certain diseases, in particular to certain fungal or bacterial diseases. Consequently, the DNA sequence encoding thanatin may be integrated with the main objective of producing plants resistant to the said diseases, thanatin being effective against fungal diseases such as those caused by Cercospora, in particular *Cercospora beticola*, Cladosporium, in particular *Cladosporium herbarum*, Fusarium, in particular *Fusarium culmorum* or *Fusarium graminearum* or by Phytophthora, in particular *Phytophthora cinnamomi*.

The chimeric gene may also advantageously comprise at least one selectable marker, such as one or more herbicide tolerance genes.

The DNA sequence encoding thanatin may also be integrated as a selectable marker during the transformation of plants with other sequences encoding other peptides or proteins of interest such as, for example, herbicide tolerance genes.

Such herbicide tolerance genes are well known to a person skilled in the art and are in particular described in patent applications EP 115 673, WO 87/04181, EP 337 899, WO 96/38567 or WO 97/04103.

Of course, the transformed cells and plants according to the invention may comprise, in addiction to the sequence encoding thanatin, other heterologous sequences encoding other additional peptides capable of conferring on the plant resistance to other diseases of bacterial or fungal origin.

The other sequences may be integrated by means of the same vector comprising a chimeric gene, which comprises a first sequence encoding thanatin and at least one other sequence encoding another peptide or protein of interest.

They may also be integrated by means of another vector comprising at least the said other sequence, according to the customary techniques defined above.

The plants according to the invention may also be obtained by crossing parents, one carrying the gene according to the invention encoding thanatin, the other carrying a gene encoding at least one other peptide or protein of interest.

Among the sequences encoding other antifungal peptides, there may be mentioned that encoding drosomycin, which is described in patent application FR 2,725,992 and by Fehlbaum et al. (1994), and in the unpublished patent application FR 97 09115 filed on Jul. 24, 1997, or that encoding androctonin described in patent application FR 2,745,004 and in unpublished patent application FR 97 10362 filed on Aug. 20, 1997.

The examples below make it possible to illustrate the invention, the preparation of the sequence encoding thanatin, of the chimeric gene, of the integration vector and of the transformed plants.

EXAMPLE 1

Construction of the Chimeric Genes

All the techniques used below are standard laboratory techniques. The detailed protocols of these techniques are in particular described in Ausubel et al.

pRPa-MD-P: Creation of a Plasmid Containing the Signal Peptide of the Tobacco PR-1a Gene The two complementary synthetic oligonucleotides Oligo 1 and Oligo 2 below are hybridized at 65° C. for 5 minutes and then by slowly reducing the temperature to 30° C. for 30'.

Oligo 1 (SEQ ID NO:6): 5' GCGTCGACGC GATGGGTTTC GTGCTTTTCT CTCAGCTTCC ATCTTTCCTT CTTGTGTCTA CTCTTCTTCT TTTCC 3'

Oligo 2 (SEQ ID NO:7): 5' TCGCCGGCAC GGCAAGAGTA AGAGATCACA AGGAAAAGAA GAAGAGTAGA CACAAGAAGG AAAGATGGAA GC 3'

After hybridization between Oligo 1 and Oligo 2, the DNA remaining single-stranded serves as a template for the Klenow fragment of polymerase I of *E. coli* (under the standard conditions recommended by the manufacturer (New England Biolabs)) for the creation of the double-stranded oligonucleotide starting from the 3' end of each oligo. The double-stranded oligonucleotide obtained is then digested with the restriction enzymes SacII and NaeI and cloned into the plasmid pBS II SK(−) (Stratagene) digested with the same restriction enzymes. A clone is then obtained comprising the region encoding the signal peptide of the tobacco PR-1a gene (SEQ ID NO 3).

pRPA-PS-PR1a-than: Creation of a Sequence Encoding Thanatin Fused to the Signal Peptide PR-1a without a Nontranscribed Region in 3'

The two synthetic oligonucleotides with complementary sequences Oligo 3 and Oligo 4 based on the operating conditions described for pRPA-MD-P.

| | | |
|---|---|---|
| Oligo 3 (SEQ ID NO:8): | 5' | GGTTCCAAGA AGCCAGTGCC AATCATCTAC TGCAACAGGA CG 3' |
| Oligo 4 (SEQ ID NO:9): | 5' | CCGGATCCGT CGACACGTTC GCCTCGCCGA GCTCACATCC TCTGGCACTT ACCAGTCCTC CTGTTGCAGT AGATGATTGG CACTGGC 3' |

Figure 1:
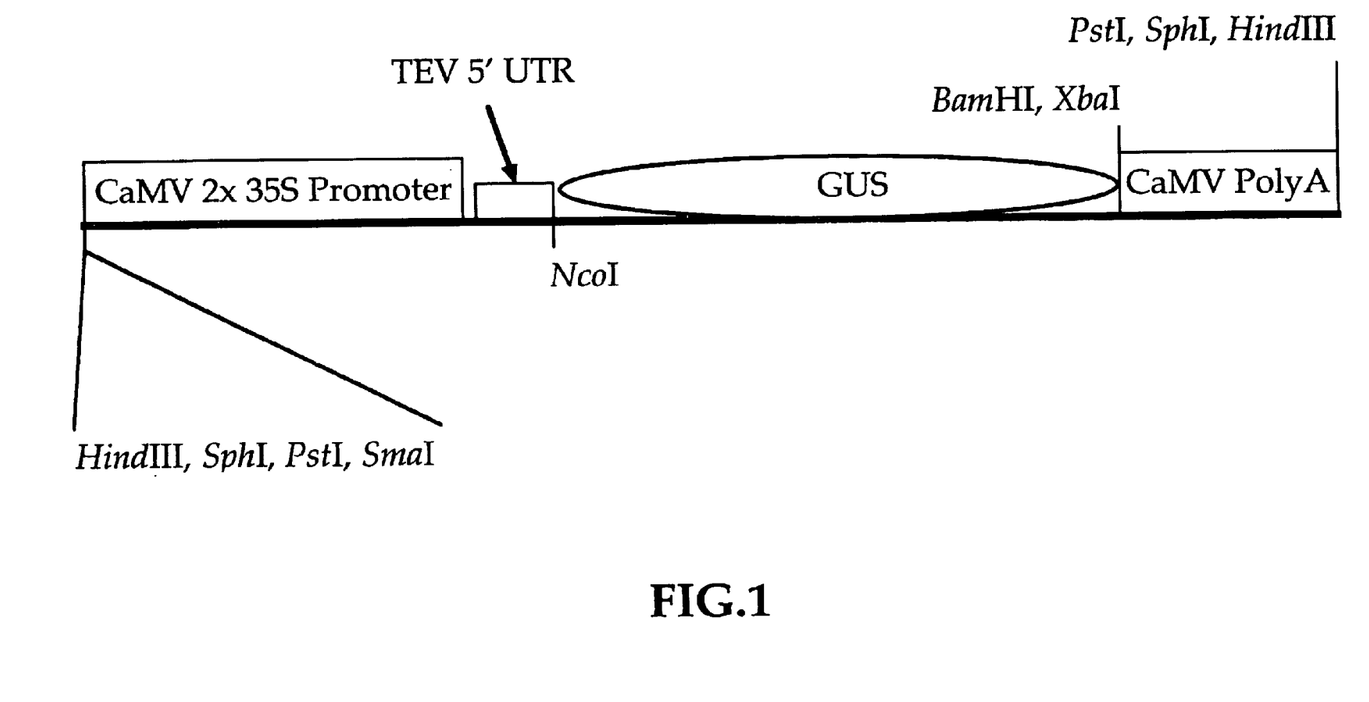
FIGS. 1 to 5 in the annex describe the schematic structures of some plasmids prepared for the construction of chimeric genes. In these figures, the different restriction sites are marked in italics.

After hybridization between Oligo 3 and Oligo 4, the DNA remaining single-stranded serves as a template for the Klenow fragment of polymerase I of *E. coli* (under the standard conditions recommended by the manufacturer (New England Biolabs)) for the creation of the double-stranded oligonucleotide starting from the 3' end of each oligo. This double-stranded oligonucleotide containing the coding part of thanatin (SEQ ID NO 1) is then directly cloned into the plasmid pRPA-MD-P which has been digested with the restriction enzyme NaeI. The correct orientation of the clone obtained is checked by sequencing. A clone is then obtained comprising the region encoding the fusion protein PR-1a-thanatin situated between the NcoI restriction sites at the N-terminal end and the ScaI, SacII and BamHI restriction sites at the C-terminal end (SEQ ID NO 4).

pRPA-RD-229: Creation of an Expression Vector in Plants Comprising the Sequence Encoding the Fusion Protein PR-1a-thanatin The plasmid pRTL-2 GUS, derived from the plasmid pUC-19, was obtained from Dr Jim Carrington (Texas A&M University, not described). This plamid, whose schematic structure is represented in FIG. 1, contains the double CaMV 35S promoter isolated from the cauliflower mosaic virus (CaMV 2×35S promoter, Odell et al., 1985) which directs the expression of an RNA containing [lacuna] tobacco etch virus 5' untranslated sequence (TEV 5' UTR; Carrington & Freed, 1990), the *E. coli* β-glucorinidase gene (GUS; Jefferson et al., 1987) followed by the polyadenylation site of the CaMV 35S RNA (CaMV polyA; Odell et al., 1985).

Figure 2:
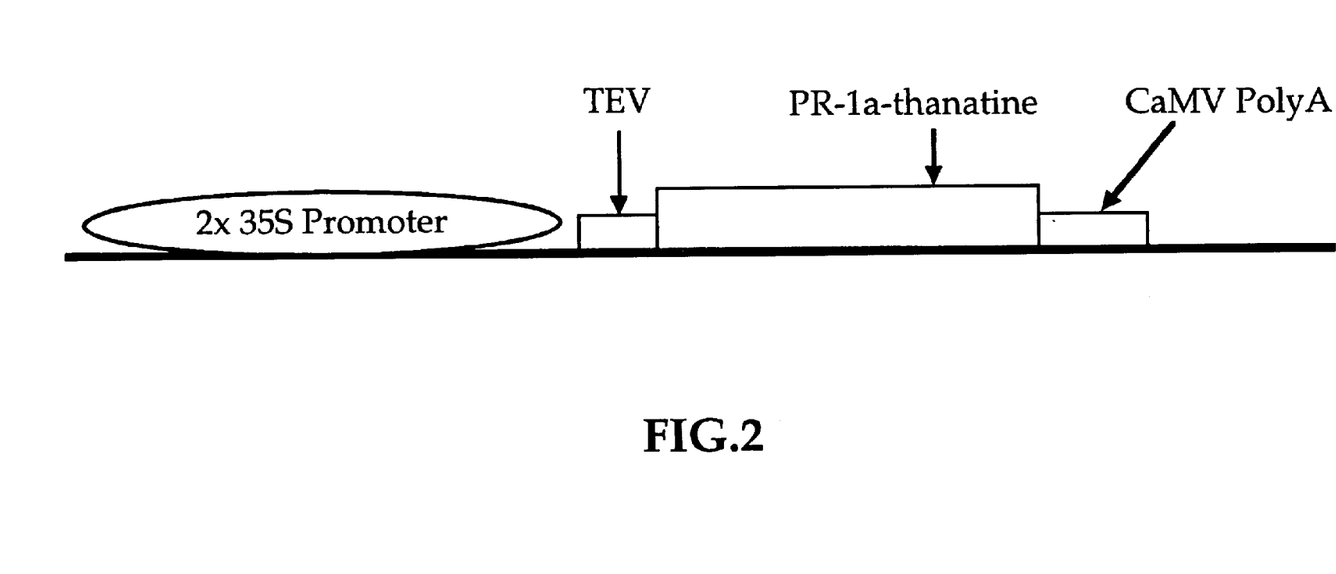

The plasmid pRTL-2 GUS is digested with the restriction enzymes NcoI and BamHI, and the large DNA fragment is purified. The plasmid pRPA-PS-PR1a-than is digested with the restriction enzymes NcoI and BamHI, and the small DNA fragment containing the region encoding the fusion protein PR-1a-thanatin is purified. The two DNA fragments purified are then ligated together in an expression cassette in plants which synthesizes a PR-1a-thanatin fusion protein. The schematic structure of this expression cassette is represented in FIG. 2. "PR-1a-thanatin" represents the coding region for the fusion protein PR-1a-thanatin of pRPA-RD-230. The thanatin is transported to the extracellular matrix of the plant by the action of the signal peptide PR-1a.

pRPA-RD-195: Creation of a Plasmid Containing a Modified Multiple Cloning Site

The plasmid pRPA-RD-195 is a plasmid derived from pUC-19 which contains a modified multiple cloning site. The complementary synthetic oligonucleotides Oligo 5 and Oligo 6 below are hybridized and made double-stranded according to the procedure described for pRPA-MD-P.

| | | |
|---|---|---|
| Oligo 5 (SEQ ID NO:10): | 5' | AGGGCCCCCT AGGGTTTAAA CGGCCAGTCA GGCCGAATTC GAGCTCGGTA CCCGGGGATC CTCTAGAGTC GACCTGCAGG CATGC 3' |
| Oligo 6 (SEQ ID NO:11): | 5' | CCCTGAACCA GGCTCGAGGG CGCGCCTTAA TTAAAAGCTT GCATGCCTGC AGGTCGACTC TAGAGG 3' |

Figure 3:
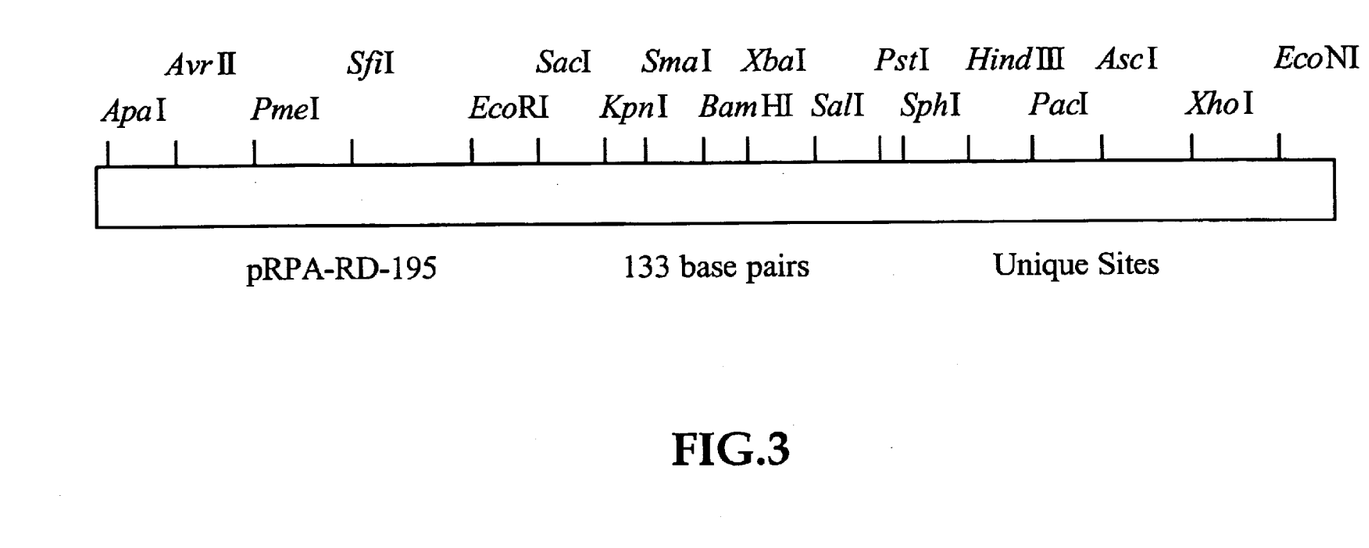

The double-stranded oligonucleotide obtained is then ligated into pUC-19 which has been previously digested with the restriction enzymes EcoRI and HindIII and made blunt ended using the Klenow fragment of DNA polymerase I of *E. coli*. A vector is obtained containing multiple cloning sites in order to facilitate the introduction of expression cassettes into an *Agrobacterium tumefaciens* vector plasmid. The schematic structure of this multiple cloning site is represented in FIG. 3.

pRPA-RD-232: Introduction of the PR-1a-thanatin Expression Cassette of pRPA-RD-229 Into pRPA-RD-195

The plasmid pRPA-RD-230 is digested with the restriction enzyme HindIII. The DNA fragment containing the PR-1a-thanatin expression cassette is purified. The purified fragment is then ligated into pRPA-RP-195 which has previously been digested with the restriction enzyme HindIII and dephosphorylated with calf intestinal phosphatase.

pRPA-RD-174: Plasmid Derived from pRPA-BL-150A (EP 0,508,909) Containing the Bromoxynil Tolerance Gene of pRPA-BL-237 (EP 0,508,909)

The bromoxynil tolerance gene is isolated from pRPA-BL-237 by a PCR gene amplification. The fragment obtained is blunt-ended and is cloned into the EcoRI site of pRPA-BL-150A which has been made blunt-ended by the action of Klenow polymerase under standard conditions. An *Agrobacterium tumefaciens* vector is obtained which contains the bromoxynil tolerance gene close to its right border, a kanamycin tolerance gene close to its left border and a multiple cloning site between these two genes.

Figure 4:
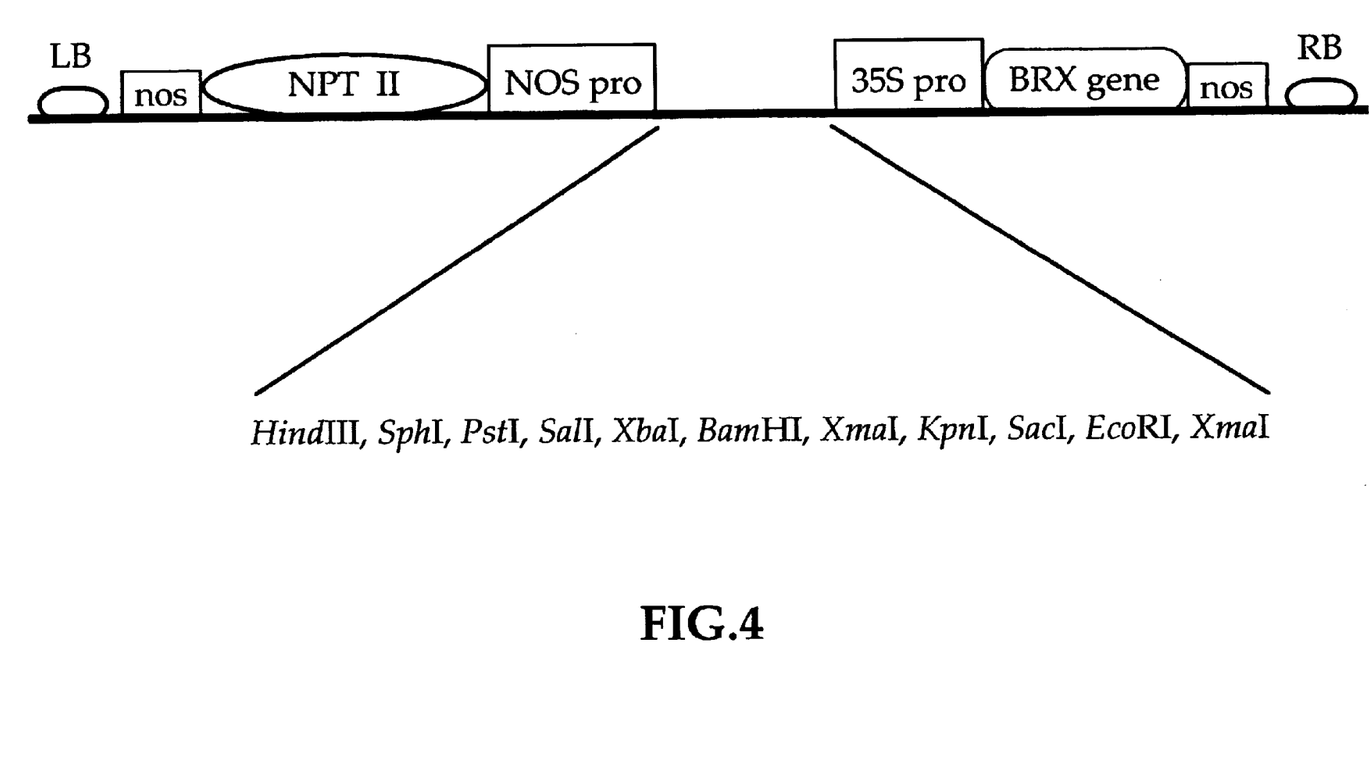

The schematic structure of pRPA-RD-174 is represented in FIG. 4. In this figure, "nos" represents the *Agrobacterium tumefaciens* nopaline synthase polyadenylation site (Bevan et al., 1983), "NOS pro" represents the *Agrobacterium tumefaciens* nopaline synthase promoter (Bevan et al., 1983), "NPT II" represents the neomycin phosphotransferase gene of the *E. coli* Tn5 transposon (Rothstein et al., 1981), "35S pro" represents the 35S promoter isolated from the cauliflower mosaic virus (Odell et al., 1985), "BRX" represents the nitrilase gene isolated from K. ozaenae (Stalker et al., 1988), and "RB" and "LB" represent respectively the right and left borders of the sequence of an *Agrobacterium tumefaciens* Ti plasmid.

pRPA-RD-184: Addition of a New Unique Restriction Site Into pRPA-RD-174

The complementary synthetic oligonucleotides Oligo 7 and Oligo 8 below are hybridized and made double-stranded according to the procedure described for pRPA-MD-P.

| | | |
|---|---|---|
| Oligo 7 (SEQ ID NO:12): | 5' | CCGGCCAGTC AGGCCACACT TAATTAAGTT TAAACGCGGC CCCGGCGCGC CTAGGTGTGT GCTCGAGGGC CCAACCTCAG TACCTGGTTC AGG 3' |
| Oligo 9 (SEQ ID NO:13): | 5' | CCGGCCTGAA CCAGGTACTG AGGTTGGGCC CTCGAGCACA CACCTAGGCG CGCCGGGGCC GCGTTTAAAC TTAATTAAGT GTGGCCTGAC TGG 3' |

The double-stranded oligonucleotide hybridized (95 base pairs) is purified after separation on agarose gel (3% Nusieve, FMC). The plasmid pRPA-RD-174 is digested with the restriction enzyme XmaI, and the large DNA fragment is purified. The two DNA fragments obtained are then ligated.

A plasmid derived from pRPA-RD-174 is obtained comprising other restriction sites between the bromoxynil tolerance gene and the selectable marker kanamycin gene.

Figure 5:
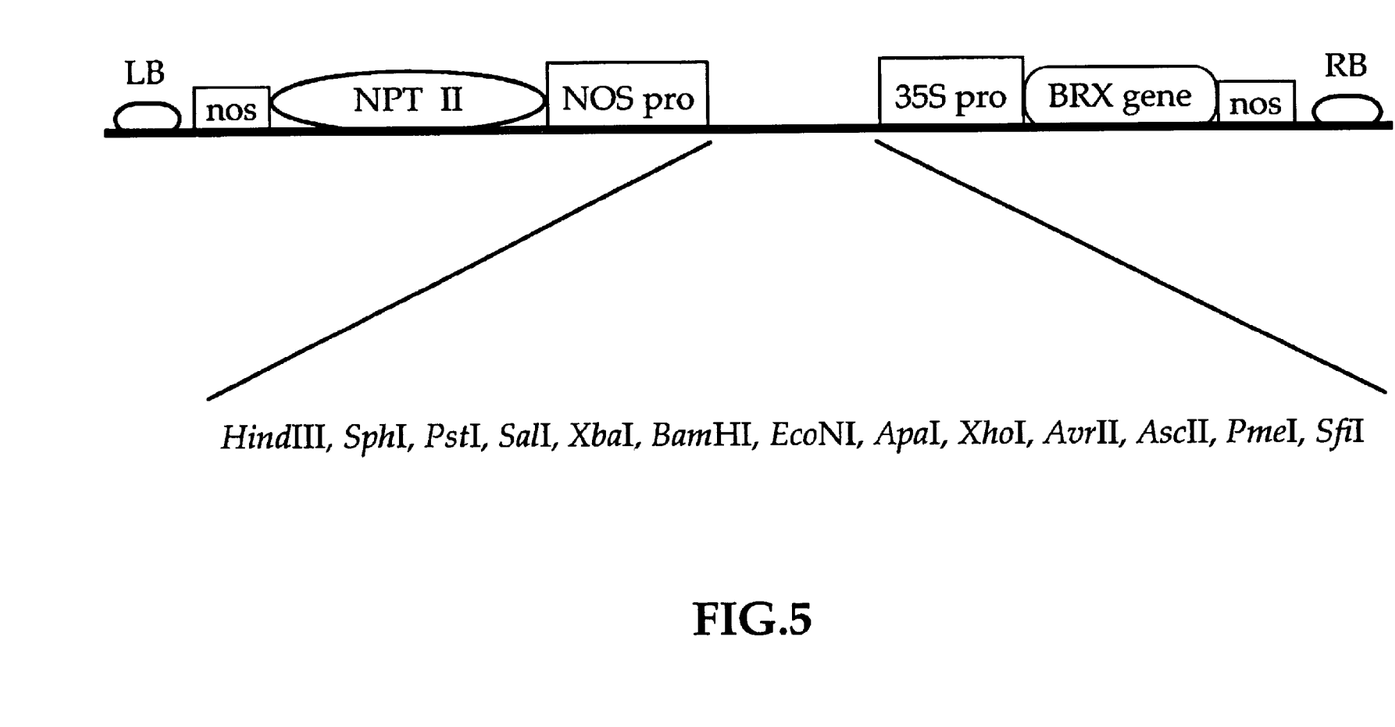

The schematic structure of the plasmid pRPA-RD-184 is represented in FIG. 5 where the terms "nos", "NPT II", "NOS pro", "35S pro", "BRX gene", "RB" and "LB" have the same meaning as in FIG. 4.

pRPA-RD-235: Creation of an *Agrobacterium tumefaciens* Vector Containing the Gene Construct Encoding Thanatin Directed Towards the Extracellular Matrix The plasmid pRPA-RD-232 is digested with the restriction enzymes PmeI and AscI, and the DNA fragment containing the gene for PR-1a-thanatin is purified. The plasmid pRPA-RD-184 is digested with the same restriction enzymes. The DNA fragment containing the PR-1a-thanatin expression cassette is then ligated into pRPA-RD-184. An *Agrobacterium tumefaciens* vector is thus obtained containing the sequence encoding the fusion protein PR-1a-thanatin which leads to the expression of thanatin in the plant's extracellular matrix.

EXAMPLE 2

Herbicide Tolerance of Transformed Tobaccos

2.1—Transformation

The vector pRPA-RD-235 is introduced into the *Agrobacterium tumefaciens* EHA101 strain (Hood et al., 1987) carrying the cosmid pTVK291 (Komari et al., 1986). The transformation technique is based on the procedure of Horsch et al. (1985).

2.2—Regeneration

The regeneration of the tobacco PBD6 (origin SEITA France) from foliar explants is carried out on a Murashige and Skoog (MS) basal medium comprising 30 g/l of sucrose as well as 200 $\mu$g/ml of kanamycin. The foliar explants are removed from plants cultivated in a greenhouse or in vitro and regenerated according to the foliar disc technique (Horsh et al., 1985) in three successive stages: the first comprises the induction of shoots on a medium supplemented with 30 g/l of sucrose containing 0.05 mg/l of naphthylacetic acid (NAA) and 2 mg/l of benzylaminopurine (BAP) for 15 days. The shoots formed during this stage are then developed for 10 days by cultivating on an MS medium supplemented with 30 g/l of sucrose but containing no hormones. Next, the developed shoots are removed and they are cultivated on an MS rooting medium with half the content of salts, vitamins and sugar and containing no hormone. After about 15 days, the rooted shoots are transferred into the soil.

2.3—Bromoxynil Tolerance

Twenty transformed plants were regenerated and transferred into a greenhouse for the pRPA-RD-235 construct. These plants were then treated in a greenhouse at the 5-leaf stage with an aqueous suspension of Pardner corresponding to 0.2 kg of bromoxynil active material per hectare.

All the plants showing complete tolerance to bromoxynil are then used in various experiments which show that the expression of thanatin by the transformed plants makes them resistant to fungal attacks.

REFERENCES

F. A. Ausubel et al. (Ed. Greene). Current Protocols in Molecular Biology. Publ. Wiley & Sons.
M. Bevan et al. (1983). Nuc. Acids Res. 11: 369–385.
Carrington and Freed (1990). J. Virol. 64: 1590–1597.
Ehret-Sabatier et al. (1996). The Journal of Biological Chemistry, 271, 47, 29537–29544.
Horsch et al. (1985). Science 227: 1229–1231.
Jefferson et al. (1987). EMBO J. 6: 3901–3907.
Komari et al. (1986). J. Bacteriol. 166: 88–94.
Rothstein et al. (1981). Cold Spring Harb. Symp. Quant. Biol. 45: 99–105.
Stalker et al. (1988). J. Biol. Chem. 263: 6310–6314.
J. T. Odell et al. (1985). Nature 313: 810–812.

SEQUENCE LISTING

<160> NUMBER OF SEQ ID NOS: 14

<210> SEQ ID NO 1
<211> LENGTH: 33
<212> TYPE: DNA
<213> ORGANISM: Psodius maculiventis
<220> FEATURE:
<221> NAME/KEY: CDS
<222> LOCATION: (1)...(33)

```
<400> SEQUENCE: 1 atc atc tac tgc aac agg agg act ggt aag tgc                    33
Ile Ile Tyr Cys Asn Arg Arg Thr Gly Lys Cys
  1               5                  10

<210> SEQ ID NO 2
<211> LENGTH: 63
<212> TYPE: DNA
<213> ORGANISM: Artificial Sequence
<220> FEATURE:
<221> NAME/KEY: CDS
<222> LOCATION: (1)...(63)
<223> OTHER INFORMATION: Derived from Psodius maculiventis

<400> SEQUENCE: 2 ggt tcc aag aag cca gtg cca atc atc tac tgc aac agg agg act ggt    48
Gly Ser Lys Lys Pro Val Pro Ile Ile Tyr Cys Asn Arg Arg Thr Gly
  1               5                  10                  15 aag tgc cag agg atg                                            63
Lys Cys Gln Arg Met
              20

<210> SEQ ID NO 3
<211> LENGTH: 98
<212> TYPE: DNA
<213> ORGANISM: Artificial Sequence
<220> FEATURE:
<223> OTHER INFORMATION: Derived from Psodius maculiventis
<221> NAME/KEY: CDS
<222> LOCATION: (1)...(63)

<400> SEQUENCE: 3 ggt tcc aag aag cca gtg cca atc atc tac tgc aac agg agg act ggt    48
Gly Ser Lys Lys Pro Val Pro Ile Ile Tyr Cys Asn Arg Arg Thr Gly
  1               5                  10                  15 aag tgc cag agg atg tgagctcggc gaggcgaacg tgtcgacgga tccgg     98
Lys Cys Gln Arg Met
              20

<210> SEQ ID NO 4
<211> LENGTH: 106
<212> TYPE: DNA
<213> ORGANISM: Artificial Sequence
<220> FEATURE:
<223> OTHER INFORMATION: Derived from Psodius maculiventis
<221> NAME/KEY: CDS
<222> LOCATION: (12)...(101)

<400> SEQUENCE: 4
gcgtcgacgc c atg ggt ttc gtg ctt ttc tct cag ctt cca tct ttc ctt    50
            Met Gly Phe Val Leu Phe Ser Gln Leu Pro Ser Phe Leu
              1               5                  10 ctt gtg tct act ctt ctt ctt ttc ctt gtg atc tct cac tct tgc cgt    98
Leu Val Ser Thr Leu Leu Leu Phe Leu Val Ile Ser His Ser Cys Arg
     15                  20                  25 gcc ggcga                                                     106
Ala
 30

<210> SEQ ID NO 5
<211> LENGTH: 197
<212> TYPE: DNA
<213> ORGANISM: Artificial Sequence
<220> FEATURE:
<223> OTHER INFORMATION: Derived from Psodius maculiventis
<221> NAME/KEY: CDS
<222> LOCATION: (12)...(164)
```

```
<400> SEQUENCE: 5
gcgtcgacgc c atg ggt ttc gtg ctt ttc tct cag ctt cca tct ttc ctt      50
            Met Gly Phe Val Leu Phe Ser Gln Leu Pro Ser Phe Leu
              1               5                  10 ctt gtg tct act ctt ctt ctt ttc ctt gtg atc tct cac tct tgc cgt       98
Leu Val Ser Thr Leu Leu Leu Phe Leu Val Ile Ser His Ser Cys Arg
     15                  20                  25 gcc ggt tcc aag aag cca gtg cca atc atc tac tgc aac agg agg act      146
Ala Gly Ser Lys Lys Pro Val Pro Ile Ile Tyr Cys Asn Arg Arg Thr
 30                  35                  40                  45 ggt aag tgc cag agg atg tgagctcggc gaggcgaacg tgtcgacgga             194
Gly Lys Cys Gln Arg Met
                 50 tcc                                                                  197

<210> SEQ ID NO 6
<211> LENGTH: 75
<212> TYPE: DNA
<213> ORGANISM: Artificial Sequence
<220> FEATURE:
<223> OTHER INFORMATION: Synthetic oligonucleotide

<400> SEQUENCE: 6
gcgtcgacgc gatgggtttc gtgcttttct ctcagcttcc atctttcctt cttgtgtcta    60
ctcttcttct tttcc                                                     75

<210> SEQ ID NO 7
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 7
tcgccggcac ggcaagagta agagatcaca aggaaaagaa gaagagtaga cacaagaagg    60
aaagatggaa gc                                                        72

<210> SEQ ID NO 8
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 8
ggttccaaga agccagtgcc aatcatctac tgcaacagga cg                       42

<210> SEQ ID NO 9
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 9
ccggatccgt cgacacgttc gcctcgccga gctcacatcc tctggcactt accagtcctc    60
ctgttgcagt agatgattgg cactggc                                        87

<210> SEQ ID NO 10
<211> LENGTH: 85
<212> TYPE: DNA
```

```
<213> ORGANISM: Artificial Sequence
<220> FEATURE:
<223> OTHER INFORMATION: Synthetic oligonucleotide

<400> SEQUENCE: 10
agggccccct agggtttaaa cggccagtca ggccgaattc gagctcggta cccggggatc      60
ctctagagtc gacctgcagg catgc                                           85

<210> SEQ ID NO 11
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 11
ccctgaacca ggctcgaggg cgcgccttaa ttaaaagctt gcatgcctgc aggtcgactc      60
tagagg                                                                66

<210> SEQ ID NO 12
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 12
ccggccagtc aggccacact taattaagtt taaacgcggc cccggcgcgc ctaggtgtgt      60
gctcgagggc ccaacctcag tacctggttc agg                                  93

<210> SEQ ID NO 13
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 13
ccggcctgaa ccaggtactg aggttgggcc ctcgagcaca cacctaggcg cgccggggcc      60
gcgtttaaac ttaattaagt gtggcctgac tgg                                  93

<210> SEQ ID NO 14
<211> LENGTH: 13
<212> TYPE: PRT
<213> ORGANISM: Artificial Sequence
<220> FEATURE:
<223> OTHER INFORMATION: Derived from thanatin
<221> NAME/KEY: VARIANT
<222> LOCATION: (1)...(1)
<223> OTHER INFORMATION: Variable residue
<221> NAME/KEY: VARIANT
<222> LOCATION: (13)...(13)
<223> OTHER INFORMATION: Variable residue

<400> SEQUENCE: 14

Xaa Ile Ile Tyr Cys Asn Arg Arg Thr Gly Lys Cys Xaa
1               5                   10

NY02:356486.1
```

What is claimed is:

1. An isolated nucleic acid comprising a nucleic acid sequence encoding a thanatin peptide which comprises the amino acid sequence of Formula I Xaa-Ile-Ile-Tyr-Cys-Asn-Arg-Arg-Thr-Gly-Lys-Cys-Xaa (SEQ ID NO:14)   (I)

in which
  Xaa at position 1 represents a variable number of 1–10 amino acid residues selected from the group consisting of Gly, Ser, Lys, Pro and Val; and
  Xaa at position 13 represents a variable number of 1–5 amino acid residues selected from the group consisting of Gln, Arg, and Met.

2. The isolated nucleic acid of claim 1, wherein the nucleic acid is DNA.

3. The isolated nucleic acid of claim 2, wherein the nucleic acid is selected from the group consisting of the nucleic acid of SEQ ID NO:1 and the nucleic acid fully complementary to SEQ ID NO:1.

4. The isolated nucleic acid of claim 2, wherein the nucleic acid is selected from the group consisting of the nucleic acid of SEQ ID NO:2 and the nucleic acid fully complementary to SEQ ID NO:2.

5. The isolated nucleic acid of claim 1 further comprising a second nucleic acid, wherein said second nucleic acid encodes a signal peptide or a transit peptide and is operably linked to the first nucleic acid.

6. The isolated nucleic acid of claim 5, wherein the signal peptide encoded by the second nucleic acid is the signal peptide from the tobacco PR-1a gene.

7. The isolated nucleic acid of claim 1, wherein the nucleic acid sequence is selected from the group consisting of the nucleic acid of SEQ ID NO:5, nucleotides 12 to 164 of SEQ ID NO:5, the nucleic acid fully complementary to SEQ ID NO:5, and the nucleic acid fully complementary to nucleotides 12 to 164 of SEQ ID NO:5.

8. The isolated nucleic acid of claim 7, wherein the nucleic acid comprises nucleotides 12 to 164 of SEQ ID NO:5.

9. A chimeric gene comprising a coding sequence operably linked to at least one heterologous regulatory element, wherein said coding sequence comprises a nucleic acid sequence encoding a thanatin peptide which comprises the amino acid sequence of Formula I:

Xaa-Ile-lle-Tyr-Cys-Asn-Arg-Arg-Thr-Gly-Lys-Cys-Xaa (SEQ ID NO:14)   (I)

in which
  Xaa at position 1 represents a variable number of 1–10 amino acid residues selected from the soup consisting of Gly, Ser, Lys, Pro and Val; and
  Xaa at position 13 represents a variable number of 1–5 amino acid residues selected from the group consisting of Gln, Arg, and Met.

10. The chimeric gene of claim 9, further comprising a selectable marker gene.

11. An expression vector comprising at least one replication origin and a chimeric gene which comprises a coding sequence operably linked to at least one heterologous regulatory element, wherein said coding sequence comprises a nucleic acid encoding a thanatin peptide which comprises the amino acid sequence of Formula I:

Xaa-Ile-Ile-Tyr-Cys-Asn-Arg-Arg-Thr-Gly-Lys-Cys-Xaa (SEQ ID NO:14)   (I)

in which
  Xaa at position 1 represents a variable number of 1–10 amino acid residues selected from the group consisting of Gly, Ser, Lys, Pro and Val; and
  Xaa at position 1 represents a variable number of 1–5 amino acid residues selected from the group consisting of Gln, Arg, and Met.

12. The expression vector of claim 11, wherein said expression vector is a viral plant transformation vector.

13. The expression vector of claim 11, wherein said expression vector is a plasmid.

14. A transformed host cell comprising a chimeric gene which comprises a coding sequence operably linked to at least one heterologous regulatory element, wherein said coding sequence comprises a nucleic acid encoding a thanatin peptide which comprises the amino acid sequence of Formula I:

Xaa-Ile-Ile-Tyr-Cys-Asn-Arg-Arg-Thr-Gly-Lys-Cys-Xaa (SEQ ID NO:14)   (I)

in which
  Xaa at position 1 represents a variable number of 1–10 amino acid residues selected from the group consisting of Gly, Ser, Lys, Pro and Val; and
  Xaa at position 13 represents a variable number of 1–5 amino acid residues selected from the group consisting of Gln, Arg, and Met.

15. The transformed host cell of claim 14, wherein the transformed host cell is a plant cell.

16. A plant comprising at least one transformed plant cell of claim 15.

17. The plant of claim 16, wherein substantially all of the cells of the plant are transformed host cells of claim 15.

18. A seed of the transformed plant of claim 17, wherein the seed retains the nucleic acid.

19. A method of transforming a host cell comprising contacting the cell host cell with a chimeric gene which comprises a coding sequence operably linked to at least one heterologous regulatory element, wherein said coding sequence comprises a nucleic acid encoding a thanatin peptide which comprises the amino acid sequence of Formula I:

Xaa-Ile-Ile-Tyr-Cys-Asn-Arg-Arg-Thr-Gly-Lys-Cys-Xaa (SEQ ID NO:14)   (I)

in which
  Xaa at position 1 represents a variable number of 1–10 amino acid residues selected from the group consisting of Gly, Ser, Lys, Pro and Val; and
  Xaa at position 13 represents a variable number of 1–5 amino acid residues selected from the group consisting of Gln, Arg, and Met, under conditions that permit said cell to take up said chimeric gene.

20. The method of claim 19, wherein the host cell is a plant cell.

21. The method according to claim 20, further comprising regenerating a transformed plant from said transformed plant cell, and cultivating the transformed plant under conditions that permit expression of said chimeric gene.

22. A method of producing a transformed progeny plant comprising:
  crossing a plant having at least one gametophyte comprising a chimeric gene which comprises a coding sequence operably linked to at least one heterologous regulatory element, wherein said coding sequence comprises a nucleic acid sequence encoding the amino acid sequence of Formula I:

Xaa-Ile-Ile-Tyr-Cys-Asn-Arg-Arg-Thr-Gly-Lys-Cys-Xaa (SEQ ID NO:14)     (I)

in which
Xaa at position 1 represents a variable number of 1–10 amino acid residues selected from the group consisting of Gly, Ser, Lys, Pro and Val; and
Xaa at position 13 represents a variable number of 1–5 amino acid residues selected from the group consisting of Gln, Arg, and Met; and
cultivating the plant under conditions that permit formation of at least one seed; and
cultivating the seed under conditions that permit the seed to grow into a progeny plant,
wherein the progeny plant retains the nucleic acid.

23. The isolated nucleic acid of claim 1, wherein the nucleic acid is selected from the group consisting of the nucleic acid of SEQ ID NO:1 and the nucleic acid fully complementary to SEQ ID NO:1.

24. An isolated nucleic acid comprising a nucleic acid encoding amino acids 2–12 of SEQ ID NO:14.

25. A isolated nucleic acid selected from the group consisting of the nucleic acid of SEQ ID NO:3 and the nucleic acid fully complementary to SEQ ID NO:3.

* * * * *